United States Patent
Fell et al.

(10) Patent No.: US 10,906,049 B2
(45) Date of Patent: Feb. 2, 2021

(54) SYSTEM FOR MULTI-PROCESSING AND SEPARATION OF BIOLOGICAL FLUIDS

(71) Applicant: Biosafe S.A., Nyon (CH)

(72) Inventors: Claude Fell, Nyon (CH); Julien Pierre Camisani, Preverenges (CH)

(73) Assignee: BIOSAFE S.A., Eysins (CH)

( * ) Notice: Subject to any disclaimer, the term of this patent is extended or adjusted under 35 U.S.C. 154(b) by 0 days.

(21) Appl. No.: 15/364,781

(22) PCT Filed: Jun. 2, 2015

(86) PCT No.: PCT/IB2015/054165
§ 371 (c)(1),
(2) Date: Nov. 30, 2016

(87) PCT Pub. No.: WO2015/186057
PCT Pub. Date: Dec. 10, 2015

(65) Prior Publication Data
US 2018/0111132 A1 Apr. 26, 2018

(30) Foreign Application Priority Data
Jun. 4, 2014 (CH) ...................................... 0854/14

(51) Int. Cl.
*B04B 5/04* (2006.01)
*B04B 5/10* (2006.01)
(Continued)

(52) U.S. Cl.
CPC ......... *B04B 5/0442* (2013.01); *A61M 1/3696* (2014.02); *B04B 5/0428* (2013.01);
(Continued)

(58) Field of Classification Search
CPC ... B04B 5/0407; B04B 5/0428; B04B 5/0442; B04B 11/02; B04B 13/00; B04B 2005/0485
See application file for complete search history.

(56) References Cited

U.S. PATENT DOCUMENTS 3,823,724 A * 7/1974 Davis ........................ F16K 7/00
137/15.01
6,733,433 B1 * 5/2004 Fell ...................... A61M 1/3693
435/2
(Continued)

FOREIGN PATENT DOCUMENTS

| EP | 06127019 | 5/1994 |
|---|---|---|
| EP | 0912250 B1 | 11/1999 |
| EP | 1144026 B1 | 7/2004 |

*Primary Examiner* — Timothy C Cleveland
(74) *Attorney, Agent, or Firm* — Eversheds Sutherland (US) LLP

(57) ABSTRACT

A system for the processing and separation of biological fluids into components comprises an apparatus that cooperates with a disposable set, comprising a cabinet (100) for housing a hollow centrifugal processing chamber (20) of the disposable set. The cabinet comprises a plurality of side-by-side locations (110) for receiving a corresponding plurality of centrifugal processing chambers (20) in side-by-side spaced-apart relation. Each location comprises an individual drive means (52) for driving its centrifugal processing chamber. Remotely-actuable valves (124) associated with the disposable sets are located on the apparatus' cabinet in the proximity of said locations. Valve actuation provides a display of the state of actuation of the valves (124). Selection of this state of actuation is arranged to control connection of the centrifugal processing chamber (20) of each fitted disposable set with a flexible container (200) of the same disposable set or another container, and to control connection of the centrifugal processing chambers (20) with (Continued)

flexible containers of the same or other fitted disposable sets in different combinations, in particular with series and/or parallel connections.

44 Claims, 14 Drawing Sheets

(51) Int. Cl.
    *A61M 1/36*     (2006.01)
    *B04B 11/02*     (2006.01)

(52) U.S. Cl.
    CPC ............... *B04B 5/10* (2013.01); *B04B 11/02* (2013.01); *A61M 2202/0437* (2013.01); *A61M 2202/0462* (2013.01); *B04B 2005/0485* (2013.01)

(56) References Cited

U.S. PATENT DOCUMENTS

| | | | |
|---|---|---|---|
| 6,808,633 B1 | 10/2004 | Okano et al. | |
| 2008/0153686 A1 | 6/2008 | Rochat | |
| 2009/0209402 A1 | 8/2009 | Andersson | |
| 2011/0294640 A1* | 12/2011 | Dolecek | A61M 1/3693 |
| | | | 494/1 |

* cited by examiner

SYSTEM FOR MULTI-PROCESSING AND SEPARATION OF BIOLOGICAL FLUIDS

FIELD OF THE INVENTION

The invention relates to a system for the processing and separation of biological fluids into components, the system comprising an apparatus that cooperates with a disposable set, the apparatus comprising a cabinet for housing a hollow centrifugal processing chamber of the disposable set. One application is the concentration of stem cells from umbilical cord blood. Other applications include the processing of bone marrow, apheresis, whole blood or generally all blood applications, adipose tissue and culture media. For instance, the system could process cultured cell products with focus on Lymphocyte T cells. The system can function as a chain processor including steps like concentration, gradient separation, washing, heating, cooling, fluid transfer and cell selection modes.

BACKGROUND OF THE INVENTION

EP-B-0 912 250 (C.FELL), the contents whereof are herein incorporated by way of reference, describes a system for the processing and separation of biological fluids into components, comprising a set of containers for receiving the biological fluid to be separated and the separated components, and optionally one or more additional containers for additive solutions. A hollow centrifuge processing chamber is rotatable about an axis of rotation by engagement of the processing chamber with a rotary drive unit. The processing chamber has an axial inlet/outlet for biological fluid to be processed and for processed components of the biological fluid. This inlet/outlet leads into a separation space of variable volume wherein the entire centrifugal processing of biological fluid takes place. The processing chamber comprises a generally cylindrical wall extending from an end wall of the processing chamber, this generally cylindrical wall defining therein the hollow processing chamber which occupies a hollow open cylindrical space coaxial with the axis of rotation, the axial inlet/outlet being provided in said end wall coaxial with the generally cylindrical wall to open into the hollow processing chamber. The processing chamber contains within the generally cylindrical wall an axially movable member such as a piston. The separation space of variable volume is defined in an upper part of the processing chamber by the generally cylindrical wall and by the axially movable member contained in the generally cylindrical wall of the processing chamber, wherein axial movement of the movable member varies the volume of the separation space, the movable member being axially movable within the processing chamber to intake a selected quantity of biological fluid to be processed into the separation space via the inlet before or during centrifugal processing and to express processed biological fluid components from the separation space via the outlet during or after centrifugal processing. Means are provided for monitoring the position of the movable member to thereby control the amount of intaken biological fluid and the expression of separated components. The system further comprises a distribution valve arrangement for establishing selective communication between the processing chamber and selected containers or for placing the processing chamber and containers out of communication.

According to EP-B-1144026 (Biosafe), such a system is arranged to operate in a separation and in a non-separation transfer mode, which provides greater possibilities for use of the system including new applications which were previously not contemplated, such as separation of hematopoietic stem cells and in general laboratory processing. Thus, the system can be arranged to operate such that:

in the separation mode fluids can be intaken into the processing chamber while the chamber is rotating or stationary, fluid intaken into the chamber is centrifuged and separated into components, and the separated components expressed while the chamber is rotating or, optionally, for the last separated component, while the chamber is stationary; and in the transfer mode the processing chamber intakes fluid and expresses fluid with the chamber stationary. The valve actuation arrangement is actuable to transfer amounts of fluid from one container to another via the processing chamber, by moving the member, without centrifugation or separation of the fluid into components, and the means for monitoring the position of the movable member controls the amounts of non-separated fluids transferred.

The above-mentioned known systems provide a vesatile platform for processing notably cord blood, bone marrow, apheresis, whole blood, biological specimens and adipose tissue. There is however a need to develop such a processing system able to reduce costs of both disposable kits and equipment while maintaining a competitive quality of processing and banking cord blood units. Such new system should be able to process several cord blood units in parallel in order to be competitive and reduce operating costs, by making it possible for one technician to simultaneously process several units in parallel.

US 2009/0209402 discloses a centrifugal separation system in which centrifugal chambers are mounted on radially oriented arms rotatable about a central rotatable shaft.

SUMMARY OF THE INVENTION

The system according to the invention is a dynamic and automated cell processing platform. Its cell separation capability is based on centrifugation allowing separation on density and size of blood particles. Blood components can be extracted into individual bags and are readily available for further processing. The system comprises several, for example six identical units, preferably with a central computer performing data acquisition and software controlling each unit individually. The invention provides a new biological fluid parallel processing system that will be used in combination with a specific, simplified disposable kit which provides for a maximum processing volume/cycle of, say, 220 ml. The inventive system can be operated by laboratory technicians or clinical laboratory technicians. One technician will suffice to process up to six (or more) processing units, e.g. umbilical cord blood units in parallel. Each module of the system/apparatus runs independently and asychronously with the other modules. Such arrangement of modules allow the chain processing of biological fluid where each module has a specific function to act on said biological fluid like concentration, gradient separation, heating, cooling, washing, additives transfer and cell selection.

In more detail, the invention relates to a system for the processing and separation of biological fluids into components which comprises an apparatus that cooperates with a disposable set, the apparatus comprising a cabinet for housing a hollow centrifugal processing chamber of the disposable set. The disposable set comprises: (a) a set of flexible containers for receiving biological fluid to be separated and separated components, and optionally one or more additional flexible containers for additive solutions, (b) the set of flexible containers is interconnected by tubing associated with valves for controlling the input and the extraction of fluids into or from the containers, and (c) a hollow centrifugal processing chamber rotatable about an axis of rotation and having an axial inlet/outlet for the biological fluid to be processed and for the processed components of the fluid. The processing chamber contains an axially movable member, typically a piston, which defines a separation space of variable size for receiving biological fluid. This member is axially movable to intake a selected quantity of biological fluid to be processed into the separation space via said inlet and to express processed biological fluid components from the separation space via said outlet.

The hollow centrifugal processing chamber of the disposable set is receivable in the apparatus' cabinet, each of said centrifugal processing chambers being rotatable about a central axis of rotation of the centrifugal processing chamber. The cabinet comprises drive means for rotatably driving a hollow centrifugal processing chamber received therein about the central axis of rotation of the centrifugal processing chamber, and means for monitoring the position of the axially movable member to control the amounts of intaken and extracted fluids.

According to the invention, the apparatus' cabinet comprises a plurality of side-by-side locations for receiving in the cabinet a corresponding plurality of centrifugal processing chambers in side-by-side spaced-apart relation, each of said side-by-side locations comprising an individual drive means for driving its centrifugal processing chamber about its central axis of rotation. The valves associated with the disposable sets are remotely-actuable valves located on the apparatus' cabinet in the proximity of the locations for receiving the respective centrifugal processing chambers; and the apparatus further comprises means for actuating the remotely actuable valves individually and by combinations of individual actuations, these valve-actuating means including a control panel that provides a display of the state of actuation whether open or closed of individual remotely-actuable valves, the selection of the state of actuation of the individual actuable valves being arranged to control connection of the centrifugal processing chamber of each fitted disposable set with the flexible container of the same disposable set or to another container, and to control connection of the centrifugal processing chambers with the flexible containers or other containers of several fitted disposable sets in different combinations, in particular with series and/or parallel connections.

In one example, the valve-actuation means for controlling the remotely-actuable valves associated with the central processing chambers receivable in the cabinet, is arranged to provide for:
  the individual control of the valve(s) associated with at least one disposable set, or all disposable sets whose centrifugal processing chambers are received in the cabinet, to separately control the inlet and outlet of fluid from the flexible container(s) of the or each disposable set;
  the control of the valves associated with at least two disposable sets, or of all disposable sets whose centrifugal processing chambers are received in the cabinet, to connect in series the outlet of at least one flexible container, or the outlet of all but one flexible container received in the cabinet, to the inlet of another flexible container, or vice versa;
  the control of the valves associated with at least two disposable sets, or of all disposable sets whose centrifugal processing chambers are received in the cabinet, to connect in parallel their inlets and outlets;
and any combination thereof.

In a preferred embodiment, the inventive apparatus is in combination with a plurality of disposable sets, each disposable set comprising a centrifugal processing chamber connected to tubing, the tubing being in Y-configuration with the stem of the Y connected to the centrifugal processing chamber, the extremity of one branch of the Y tubing being connected to a flexible container for biological fluids, the extremity of the other branch of the Y tubing being connectable to a container of biological fluid to be processed or to a container of additive, the two branches of the Y tubing having zones that pass though the remotely-actuable valves, said zones of the tubing being closable by actuation of the remotely actuable valves, said zones being located adjacent to where the two branches of the tubing are branched to the stem of the Y.

The disposable sets may each include manually-operable pinch valves (clamps) on the tubing, the manually-operable pinch valves being operable for making a connection of the disposable set with other containers when the disposable set is being connected in the apparatus according to the invention. The manually-operable pinch valves are openable to allow processing and transfer of fluids by the centrifugal processing chamber when the disposable set is connected in the apparatus according to the invention.

The tubing of the disposable sets is made of a flexible plastics material that is inert to biological fluids and generally made of Polyvinyl Chloride plastics or Ethylene Vinyl Acetate (EVA).

At each location for a processing chamber there can be a specific module which is part of a chain processing where each module has a dedicated role in the processing of a biological fluid, said biological fluid being sequentially transferred from modules to modules.

Preferably the valves are electro-magnetically actuable pinch valves located on a substantially flat top of the cabinet in the proximity of the locations for receiving the respective centrifugal processing chambers.

In a preferred embodiment, the top of the cabinet has on its outer surface at locations adjacent to those for receiving the processing chambers, an array of projections provided with through-openings for guiding the tubing of the flexible containers, and wherein the cabinet's top optionally comprises, in-between and adjacent to the projections of each array of projections, a visible guide line indicating a path for the tubing of the flexible container, which path passes through the projections.

In this embodiment, the top of the cabinet adjacent to each location for receiving a processing chamber preferably comprises three generally cylindrical projections, a first projection incorporating an optical line sensor, the first projection having in its top surface a diametral groove for receiving the tubing, and two second projections each incorporating an electromagnetically-actuable pinch valve, the second projections each having a lateral through-groove for receiving a tubing, the first projection and two second projections being situated on a generally Y-shaped path for the tubing along the top of the cabinet.

In another embodiment, the apparatus' cabinet has a substantially flat top and a generally upright outer wall wherein the outer wall of the cabinet comprises, in its upper part, a series of recesses in correspondence with the locations where the processing chambers are received, said recesses each being shaped and configured to receive and support a flexible container of a disposable set on the outer/upper wall of the cabinet.

In one embodiment, the apparatus' cabinet has the approximate shape of a D in horizontal section, with a curved outer wall along which and adjacent to which said locations for the processing chambers are distributed. In this embodiment, adjacent a flat rear wall of the apparatus' cabinet are two upstanding poles extending above and generally behind the cabinet, said poles having attachments for suspending bags of biological fluid to be treated or additives. Advantageously, a touch-screen command is supported between the two poles by a central post extending up from the cabinet.

In general, the apparatus' cabinet has a plurality of from four to fifteen housings for the processing chambers, for example six or twelve. However, as a minimum there must always be two.

The inventive system can be arranged to operate in a separation mode and in a non-separation transfer mode, as in EP-B-1144026. The new processing system is intended for laboratory use and is intended for use in combination with a specific disposable set. Its principle is based on centrifugal separation, allowing separation on density and size of blood particles. Blood components are collected in individual containers (flexible bags) and are readily available for further processing.

The apparatus according to the invention may incorporate a Peltier effect element for temperature control of external bags containing notably the biological fluids, in particular for cooling the biological fluids. For example, the apparatus according to the invention may incorporate a temperature control and may cooperate with the mixing system for mixing biological specimens with additives described in the as-yet unpublished PCT/IB2013/058403 (Biosafe). For instance there can be a pumping system for preparing cord blood units prior to cryopreservation. By pre-connecting an extension disposable line to 204 (FIG. 9), the extension line is inserted in a pumping system allowing to transfer biological additives like dimethyl sulfoxide (DMSO) or other biological additives to the cryopreservation bag 200. The fluid transfer is performed under a controlled temperature and constantly mixed to ensure an homogeneous mixing in the collection bag.

The processing system is composed of a plurality, typically six or more, processing units received in a central cabinet, the six units being associated with a central computer typically having a touch-screen control, the central computer performing data acquisition and with software individually controlling the processing units separately. Each processing unit is typically composed of a centrifugal chamber, a piston detection algorithm, a pinch valves system for tubing lines selection, and a spectrometric sensor for automating separation of blood elements.

Each processing unit comprises a disposable processing chamber like that described in EP-B-0 912 250 which is able to centrifuge the contents of the disposable kit's flexible bags and detect the volume of liquid/blood inside the disposable chamber. A spectromatic sensor also like that of EP-B-0 912 250 is used for automating separation of blood elements and a pinch valve system can be used to open or close a main blood bag or buffy coat bag.

The disposable kit is the only element in contact with the liquid such as cord blood being processed and is able to process a given maximum volume/cycle of liquid, say 220 ml. This capacity is of course multiplied by the number of cycles and the number of disposable sets that can be processed simultaneously by the inventive system.

The inventive system allows parallel processing of several disposable kits simultaneously. The system described hereinafter by way of example can process up to six disposable kits; however, the system can be designed to process more disposable sets if required.

Asynchronous processing is possible with several disposable kits; each biological fluid can start and stop at any time independent from other procedures.

Each procedure can have a customized processing profile. Each biological fluid can be processed with a different processing profile or sedimentation profile separately of one another.

Electromagnetically-operable pinch valves can be included for fluid aspiration or extraction from the centrifugal processing chamber. There is a possibility to add more input-output transfer bags with pinch valves or rotating motors for the centrifugal processing chamber for performing complex procedures like centrifugation with the addition of a gradient density agent.

For controlling the apparatus according to the invention, it advantageously has a central touch screen, CPU units and an acquisition system. A database system for data management can be integrated.

By connecting several chambers in parallel the volume processed can be increased and/or the processing separation time can be speeded up.

Connection of variable-sized chambers (the centrifugal processing chamber) in series allows for multiple sequential processing steps under a closed system.

The system preferably includes a portable code-bar reader that can be used to read a code bar unique to each disposable set.

The disposable sets are preferably made simpler and less expensive than existing disposable sets with stopcock valves, by replacing the stopcock valves with pinch valves.

The primary application of a cord blood parallel processing system according to the invention is an automated procedure allowing the concentration of stem cells from umbilical cord blood.

BRIEF DESCRIPTION OF DRAWINGS

The invention, and a prior art arrangement, will be further described by way of example with reference to the accompanying drawings, in which.

DETAILED DESCRIPTION

Figure 1:
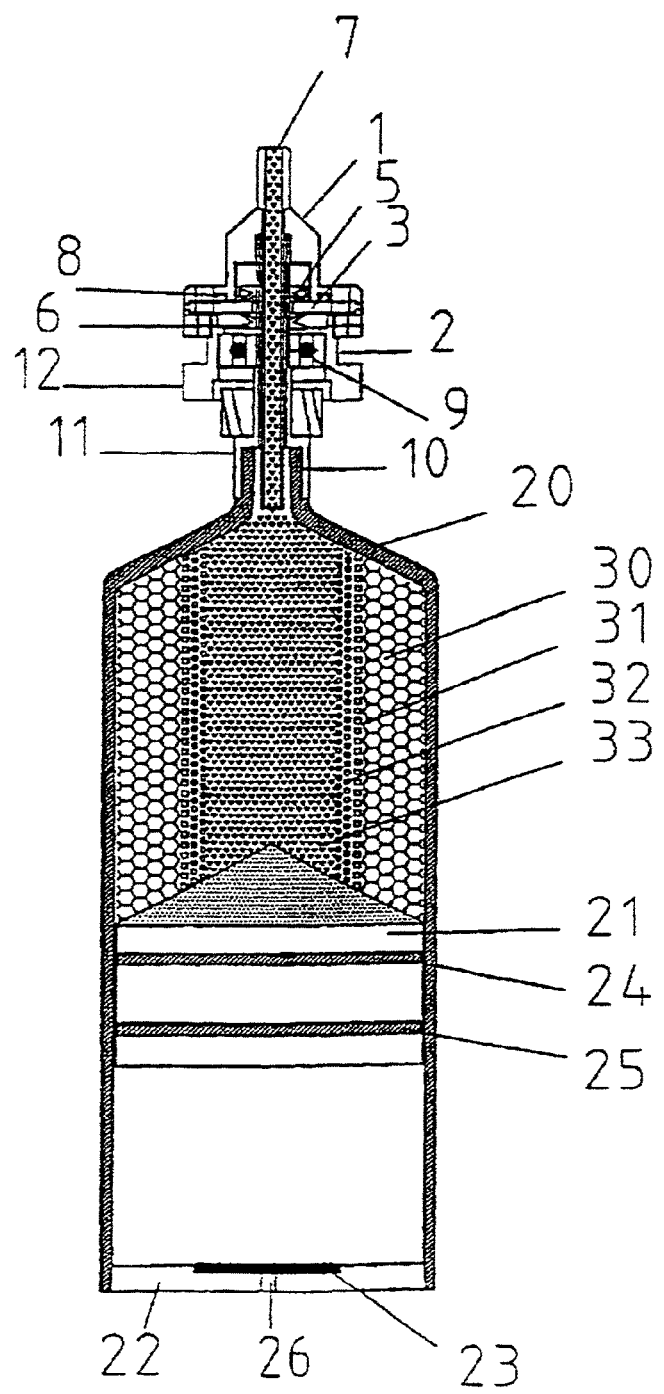
FIG. 1 is a schematic side elevation and cross-sectional view of a processing chamber according to the prior art (EP-B-0 912 250) and its rotary seal, showing the various sedimentation layers of blood components, such processing chamber being employed also in the apparatus according to the invention.

The processing chamber 20 employed with the apparatus according to the invention is in accordance with that described in EP-B-0 912 250 (C.FELL). FIG. 1 is a general view of the processing chamber 20. A rotary seal 12 is located on its upper extremity 10. The rotary seal 12 is composed of an upper body 1 and lower body 2. In between is located a friction disk 3, made of a generally low friction material like polished stainless steel or ceramic. A central tubing 7 made of biocompatible material like polycarbonate is attached to the upper body 1. An O-ring 8 ensures airtightness between the upper body 2 and friction disk 3. The rotary seal 12 is mounted on a central bush 11 fitted on the upper extremity 10 of processing chamber 20. However, central bush 11 can be an integral part of chamber 20. The gap between walls of central tubing 7 and central bush 11 is small, say 0.5 mm, to provide a high rotational impedance for stopping any liquid to reach the upper extremity of bush 11. A ball bearing 9 is mounted on bush 11 to ensure the proper alignment of the processing chamber 20 when inserted into centrifuge assembly. Two rubber seals 5,6 are located on either side of the friction disk 3, seal 5 being on the upper side and seal 6 being on the lower side. The seals 5 and 6 are of the V-seal type and ensure airtightness both in positive and negative pressure, up to at least +−0.5 bar.

Figure 2:
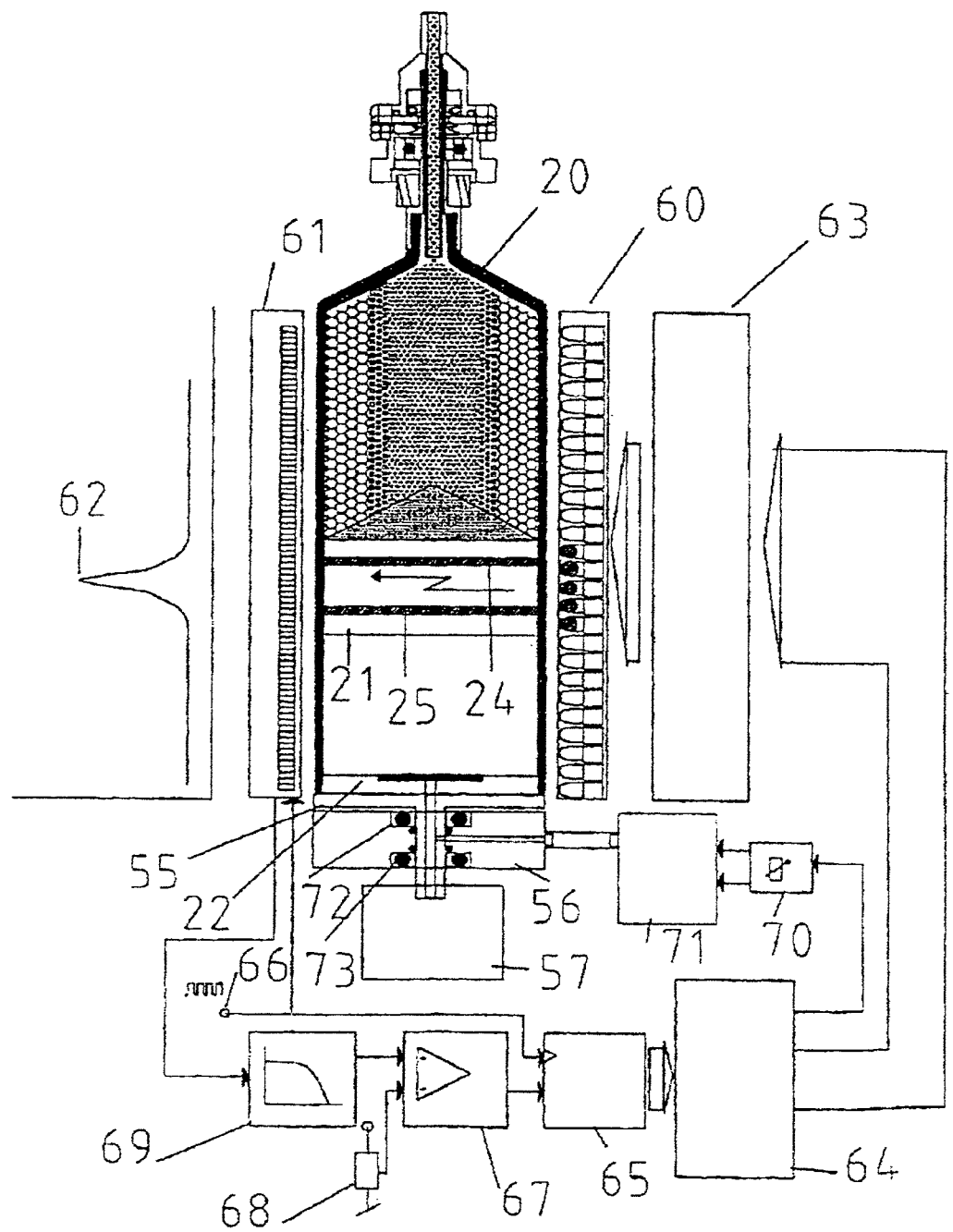
FIG. 2 is a schematic side elevation and cross-sectional view of this prior art processing chamber and its rotary seal, associated with an optical sensor for monitoring the piston sensor, and control circuitry, the optical sensor and control circuitry preferably being incorporated in the apparatus according to the invention.

The piston 21 is made of a transparent material like polycarbonate and is equipped with two O-rings 24 and 25. These O-rings are made of low friction material like silicon. The processing chamber 20 is closed on its bottom side by a cap 22 carrying a bacterial filter 23. Air can pass through central opening 26 and filter 23 in cap 22. The position of the piston 21 can be accurately monitored by an optical sensor assembly 60 and 61 (FIG. 2). Assembly 60 is made of a vertical array of LED, preferably with light emitting in the infrared spectrum to reduce disturbance from ambient light. Only the LED facing piston 21 are turned on, in order to avoid interference from the other LED. The beam of light crosses the transparent piston 21, between the two O-rings 24 and 25. A CCD ("Charge Coupling Device") linear array 61 is placed at 180° on the other side, the exposed pixels of array 61 generating a signal 62 in the form of a peak.

Signal 62 is fed to a low-pass filter 69 and the filtered signal fed to a comparator 67 which also receives from potentiometer 68 a threshold value for discriminating the filtered signal from ambient noise. The output of comparator 67 is connected to the enable gate of counter 65. Clock signal 66 is used to intake the response from each individual pixel of the CCD linear array 61, and feed this to the input of counter 65. The output of counter 65 is connected to a CPU 64 which calculates the position of piston 21 and, when required, shifts the turned-on LEDs 60 via a multiplexer/LED driver 63. Similarly, when necessary, the CPU 64 will vary the signal of compressor driver 70 that supplies compressor 71 in order to increase or decrease pressure applied below the piston 21 to control its position.

This is only one example of position sensing for the piston 21. The light source 60 could be a filament bulb, or a unique linear source of light. The CCD linear array 61 could be replaced by an array of photosensing devices. The receiving sensing device (61) could be placed also beside the emitting light device 62, the system working in reflection light from the piston 61 rather in transmittance light through the piston 21.

Figure 3:
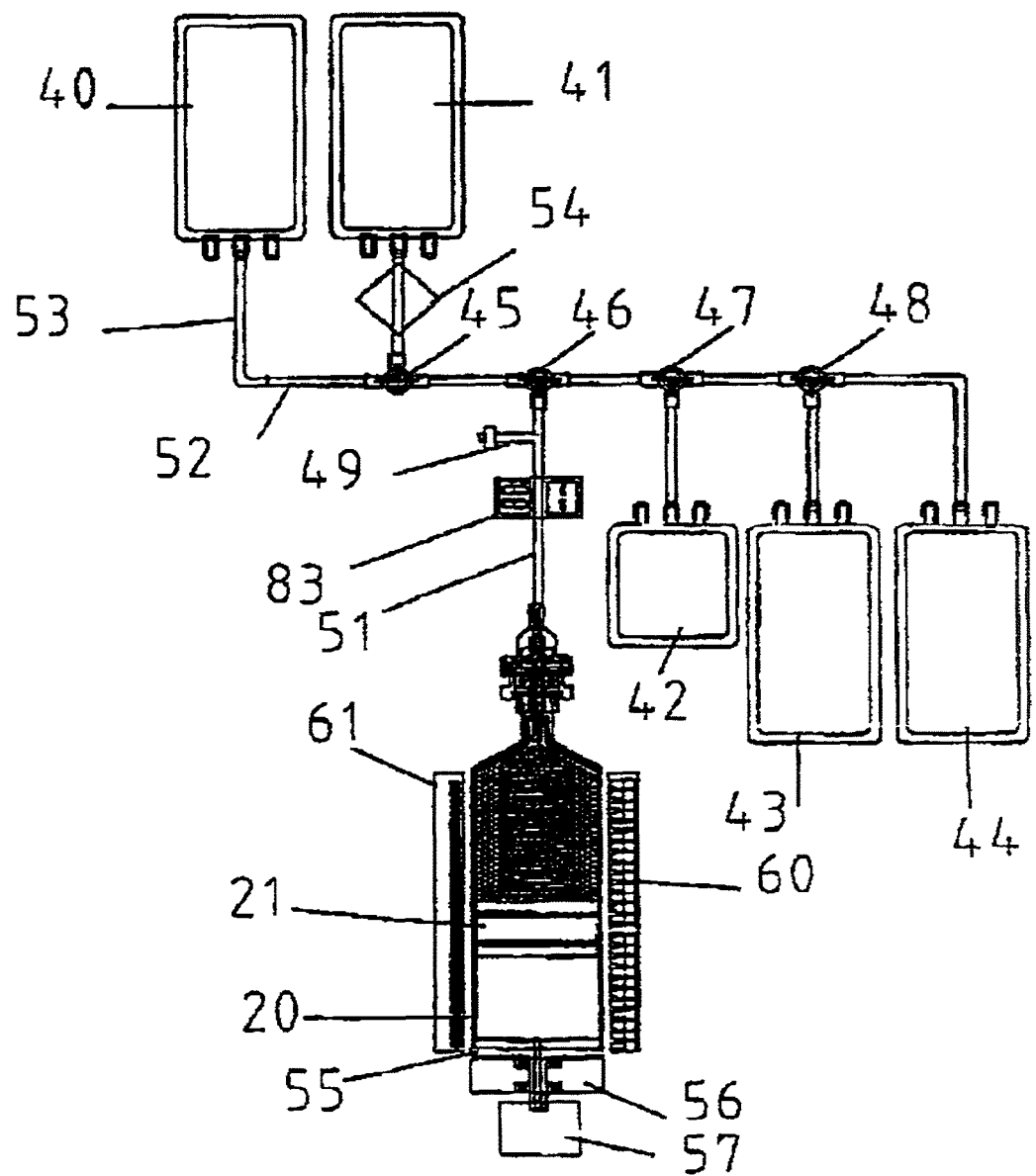
FIG. 3 illustrates in a schematic form a prior art disposable set carrying a prior-art manifold stopcock system for the processing and separation of umbilical cord blood, such disposable set being useful also in the apparatus according to the invention preferably with the stopcocks replaced by pinch valves.

The disposable set of EP-B-0 912 250 (FIG. 3) is composed of flexible bags 40-44, tubing lines connected in the prior arrangement to stopcocks 45-48, and the processing chamber 20. In this example, bag 40 contains the umbilical cord blood to process. Bag 41 contains preservative solution, generally based on a DMSO (Dimethyl Sulfoxide) solution. It is connected to the disposable set through a bacterial 0.2 micron filter 54. Bag 42 is the collection bag for the stem-cell rich product. Its plastic composition is made of a material suiting long term storage. Bag 43 is the collection bag for the plasma and bag 44 is the one for the red cells.

In the prior art arrangement of EP-B-0 912 250, an array of stopcocks was organized in a manifold to allow the connection between the different tubing lines. In the preferred embodiment of the apparatus according to the invention, the stopcocks are replaced by pinch valves which are simpler to manipulate and less expensive. Also, the prior arrangement' has two processing liquid bags for one set of disposables. In the present invention the disposable need only have one processing bag which, together with the use of pinch valves in lieu of stopcocks, considerably reduces the cost of each disposable set and hence the operating cost of the system.

Figure 4:
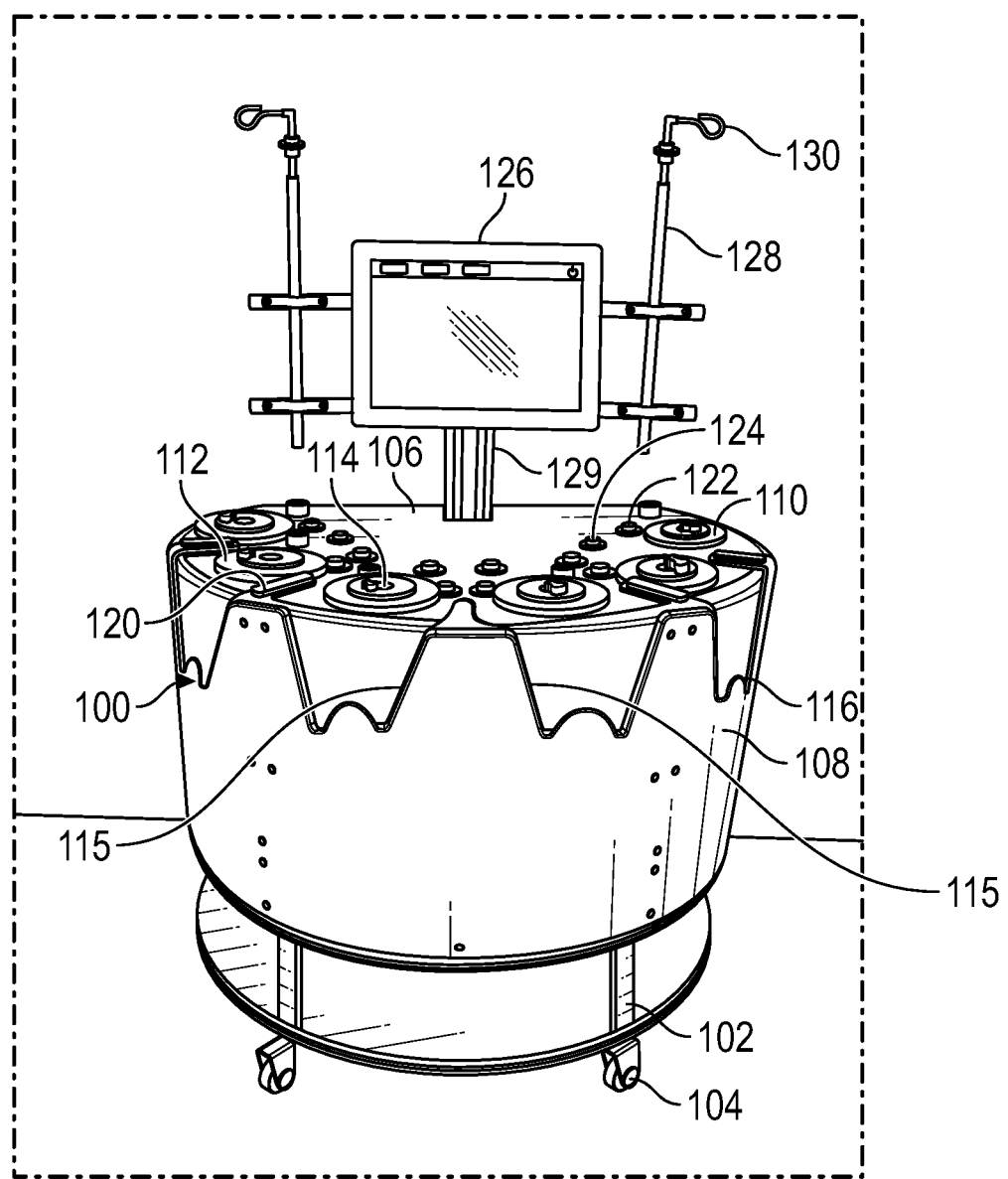
FIG. 4 is a photograph of an apparatus according to the invention seen from the front and without any disposable set attached.

FIG. 4 shows an example of an apparatus according to the invention without any disposable sets connected. The apparatus comprises a cabinet 100 mounted on a chassis 102 fitted with wheels 104, so the apparatus can easily be moved around and so that the cabinet's top 106 is at a convenient height for an operator. The cabinet 100 is approximately of D-shape in horizontal section and has an outwardly bulging front sidewall 108. In its top face 106 are six locations 110 each for receiving a centrifugal processing chamber 20 (FIG. 1) Each location 110 has a fixed flat ring 112 and a central cover 114 that can be pivoted open about a vertical axis to receive a processing chamber. These locations 110 are evenly distributed and spaced apart along the curved outer edge of top 106.

The cabinet 100 thus has an essentially flat top 106 and a generally upright outer wall 108 and this outer wall 108 comprises, in its upper part, a series of six recesses 115 in correspondence with the locations 110 where the processing chambers are received. These recesses 115 are generally flat and outwardly flared towards the top. At their bottom end, the recesses 115 have upstanding flaps 116 spaced apart from the rear wall of the recess, forming a pocket for receiving a disposable flat flexible bag of a disposable set.

Between the recesses 115, the top of sidewall 108 is extended upwardly and inwardly by a series of arms 120 which extend partly between the locations 110 to form partial separators. On the top 106 are a series of arrays of projections 122, 124 that will be further described in connection with FIGS. 6, 7 and 8.

A central post 129 extends vertically upwards from the rear of cabinet 100, this post 129 supporting a touchscreen command 126 at an adjustable height so the screen can be set at a convenient height for an operator. On either side of the touchscreen 126 are two upright poles 128 extending above and generally to the rear of cabinet 100, these poles 128 being supported by a cross-bar 132 attached to the central post 129. At their top ends, the poles 128 are fitted with hooks 130 for the attachment of blood bags or bags of other biological fluids to be processed.

Figure 5:
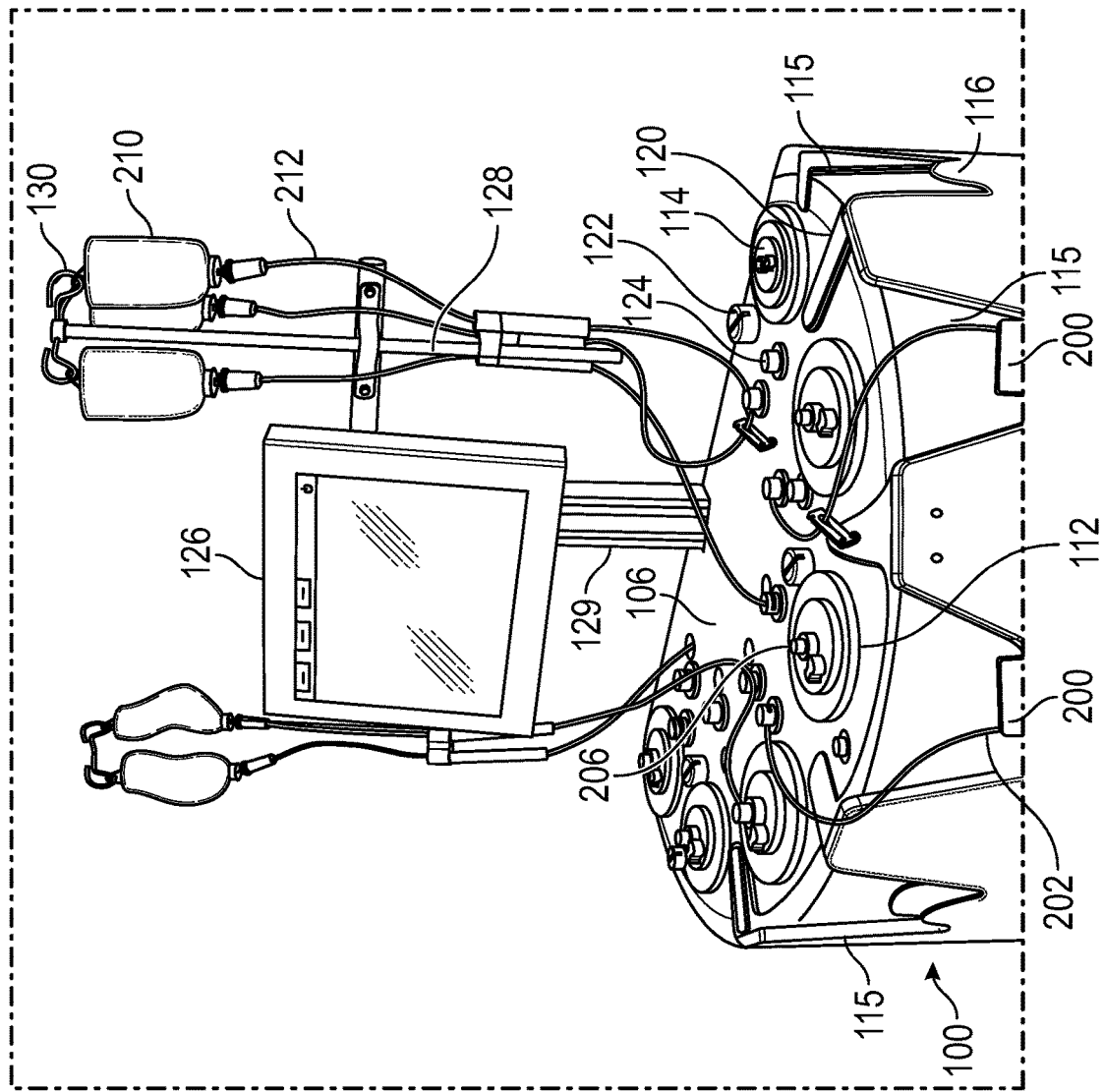
FIG. 5 is a photograph of the top part of an apparatus according to the invention seen from the front with disposable sets and blood bags attached.

FIG. 5 shows the top part of an apparatus according to the invention seen from the front, with disposable sets and blood bags attached. The disposable sets comprise a flexible pouch 200 of biological fluid to be treated/processed, for example a cryopreservation bag of blood components as described in EP-B-2 315 655, and tubing in Y-configuration, with one branch 202 leading from a fluid processing bag and another branch connectable/connected to tubing 212 leading to blood bags 210, and an end part connected to a centrifugal processing chamber of which only the top connector 206 is visible. It can be seen on FIG. 5 that the flexible pouches 200 are stored in the pockets 116 of recesses 115 and the tubing 202 leads up to the top of cabinet 106 in a configuration explained in conjunction with FIGS. 6 and 7.

Figure 6:
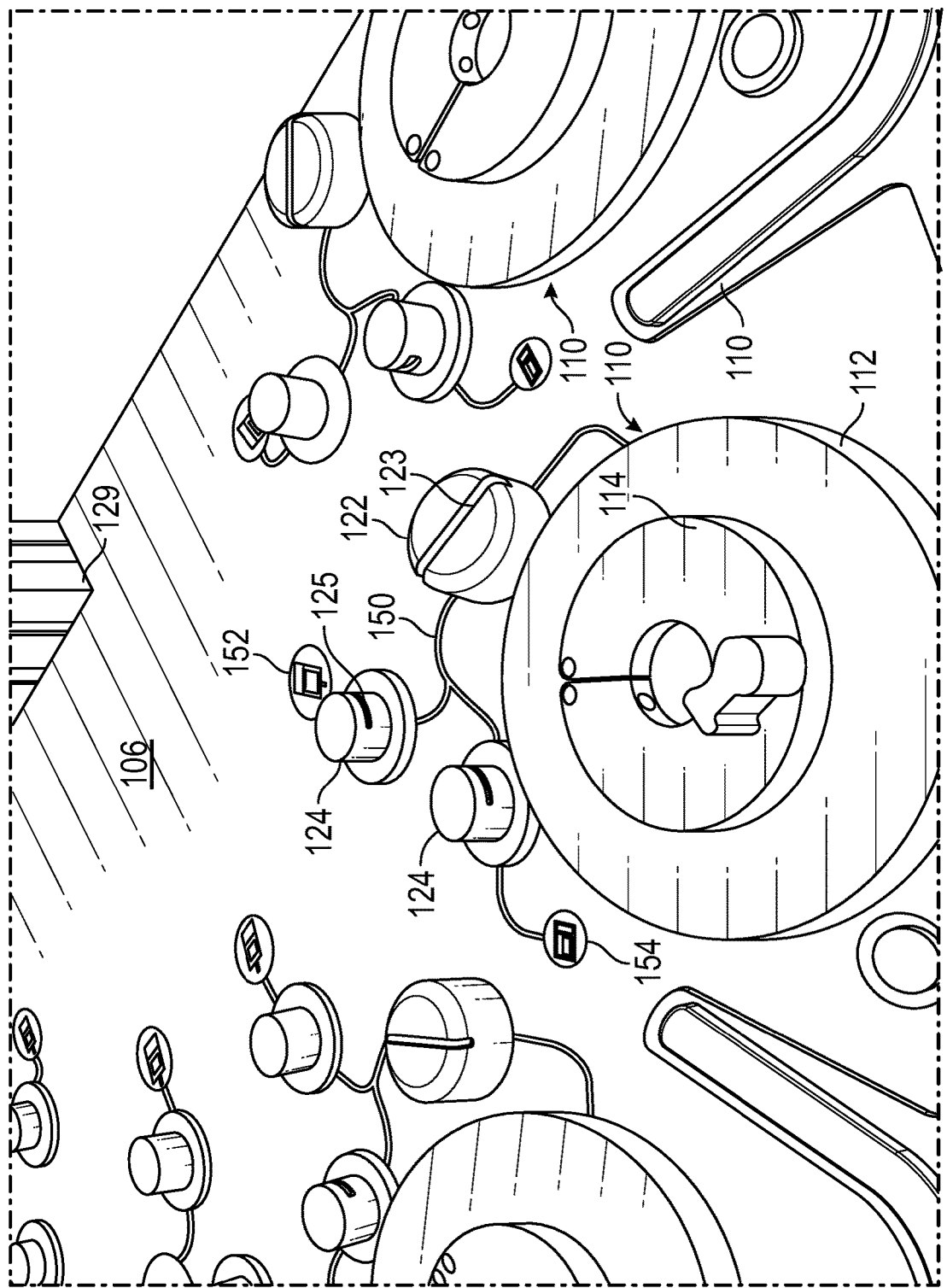
FIG. 6 is a photograph in enlarged view of the top of the cabinet of an apparatus according to the invention without any disposable set attached.

FIG. 6 shows the layout of the cabinet top 106 before disposable sets are connected. As shown in FIG. 6, the cabinet top 106 has at locations adjacent the locations 110 for receiving the centrifugal processing chambers, i.e. inside the rings 112 and at the positions of covers 114, an array of projections 122, 124 for guiding and holding the tubing of the disposable sets. Each array comprises a first projection 122 with a diametral slot in its top surface for receiving the tubing, and two second projections 124 in the form of a cylinder with a flat face in which there is a horizontal groove for receiving the tubing. The first projection 122 houses an optical line sensor. The second projections 124 each house an electromagnetically-operable pinch valve. As shown, in-between and adjacent to the projections 22, 24 is a visible guide line 150 in generally Y-shape, indicating a path for the tubing of the disposable set. At the ends of the two branches of the Y-shaped path 150 are pictograms illustrating the intended connection, pictogram 152 schematically representing a blood bag, and pictogram 154 schematically representing a bag of biological fluid to be treated, like a cryopreservation bag.

The electromagnetically-operable pinch valves 124 are a known type of solenoid-operated device designed to open and close tubing. Suitable pinch valves are for instance available under the trademark Bio-Chem Valve, see www.biochemfluidics.com. In such valves energizing the solenoid retracts a valve plunger either to open the tubing or closes the tubing. De-energizing the solenoid allows a spring to push the plunger back to its original closed or open position. Energizing and de-energizing the solenoid can be controlled from a distance, namely from the inventive apparatus' control panel 126.

Figure 7:
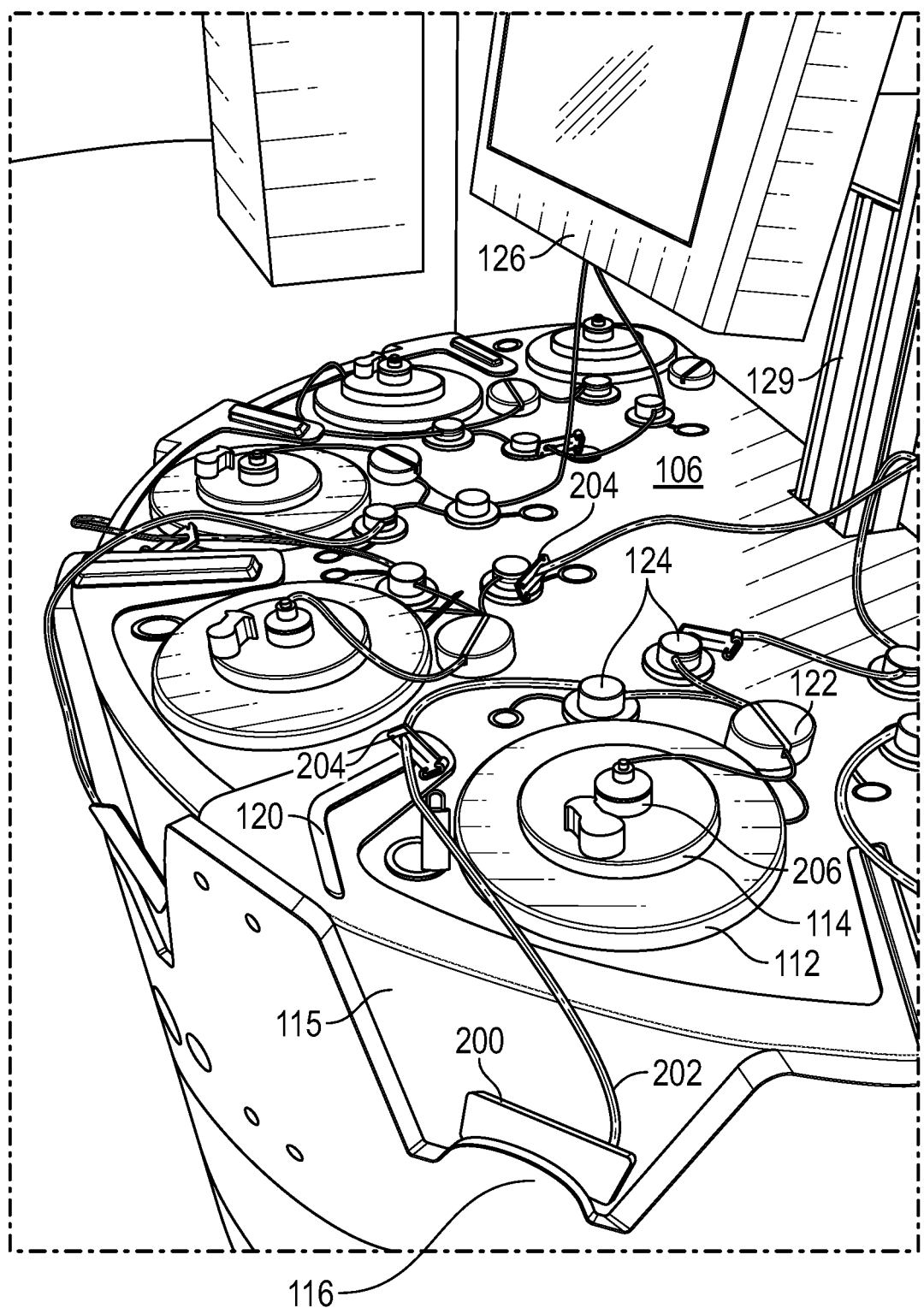
FIG. 7 is a photograph in perspective of the top of the cabinet of an apparatus according to the invention with disposable sets attached.
Figure 8:
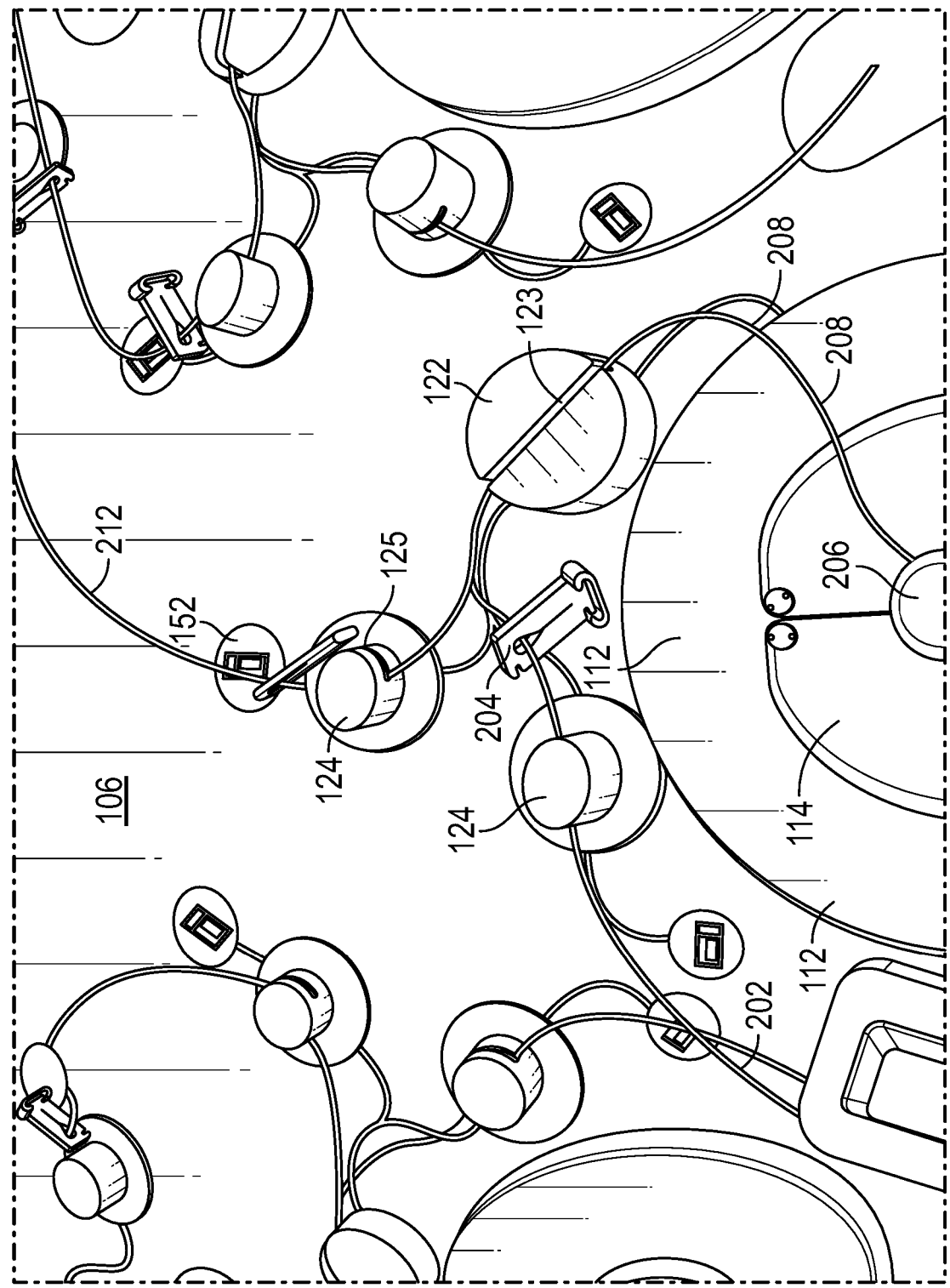
FIG. 8 is a photograph in enlarged view of the top of the cabinet of an apparatus according to the invention with disposable sets attached

FIG. 7 shows the connections of the disposable sets on a cabinet top 106 and FIG. 8 shows a detail. The disposable flexible containers 200 are lodged in the pockets 116 of recesses 115, and from there a first branch 202 of their tubing extends up to the cabinet top 106 to the first projection 124 (electromagnetically operable pinch valve) in whose groove 125 the branch 202 of the disposable tubing is inserted and passes. The photographs show a number of manually-operable plastic pinch valves 204; however, these are only for use by the operator when connecting the disposable tubing to the tubing 212 from the blood bags, when the apparatus is being set up. The manual pinch valves 204 play no part in the automated multiprocessing operation of the apparatus according to the invention. During operation the manual pinch valves 204 remain idle.

The first branch 202 of the disposable tubing stops short of the first projection 122, whereas its second branch 212 passes through the other second projection 124 and extends towards the blood bags 210 to which it is connected in a preliminary operation. The common branch 208 of the disposable tubing leading to the connector 206 of the centrifugal processing chamber 20 is inserted in the groove 123 and passes through the first projection 122, i.e. the optical sensor.

Figure 9:
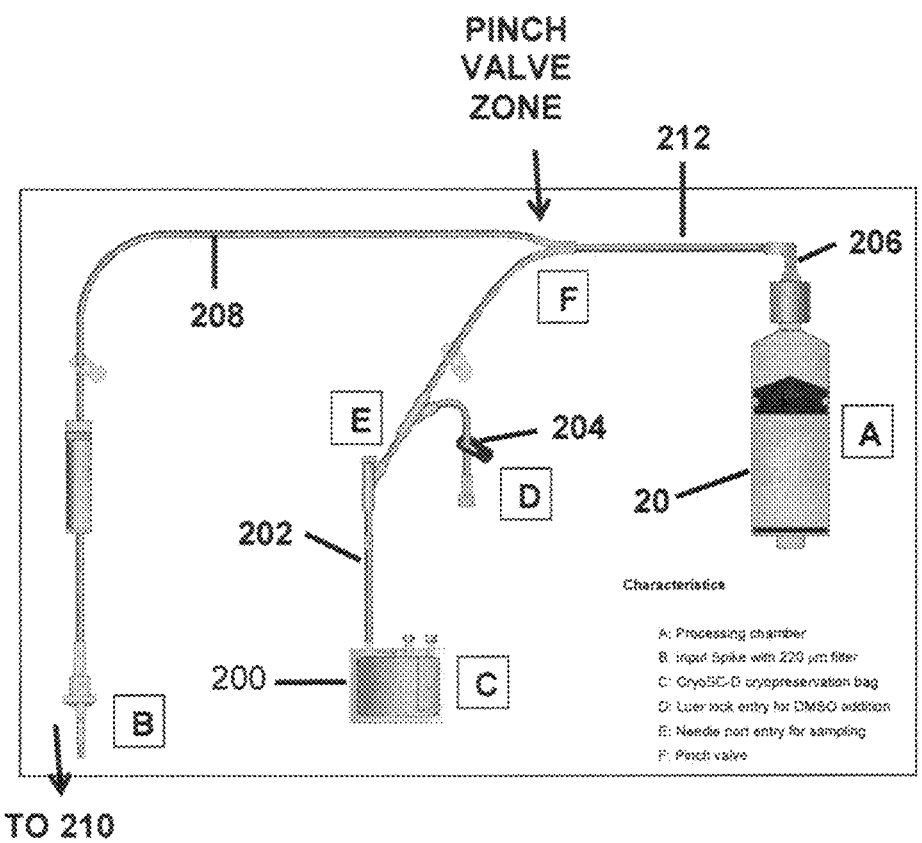
FIG. 9 is a schematic view of a disposable set to be employed with the apparatus according to the invention.

FIG. 9 shows a disposable set usable with the apparatus according to the invention. The disposable set comprises a bag 200 for a biological fluid to be collected and/or processed, for instance a cryopreservation bag of EP-B-2 315 655, connected to a centrifugal processing chamber 20 by tubing 202, 208 and 212 in Y-configuration The common branch 212 is connected to the centrifugal processing chamber 20 and the branch 202 is connected to the bag 200. Branch 208 is intended to lead to a spike leading to a bag 210 containing processed fluid, blood or another biological fluid, or an additive such as DMSO. and for this purpose has a special connector at its end. In the region where the branches 202 and 208 join is a pinch valve zone, where the branches will pass though the elecromagnetic pinch valves 124, as described above. This disposable set can be manufactured in one piece, so the operator of the inventive system does not need to make connections apart from an initial set up to connect branch 208 to a blood bag. As mentioned previously, this disposable set enables the inventive system to be operated with low operating cost on account of the use of simple electromagnetically-operated pinch valves 124 and the limitation to one processing bag. The inventive system can operate with this simplified disposable set and achieve multiprocessing due to the many possibilities available.

Figure 15A:
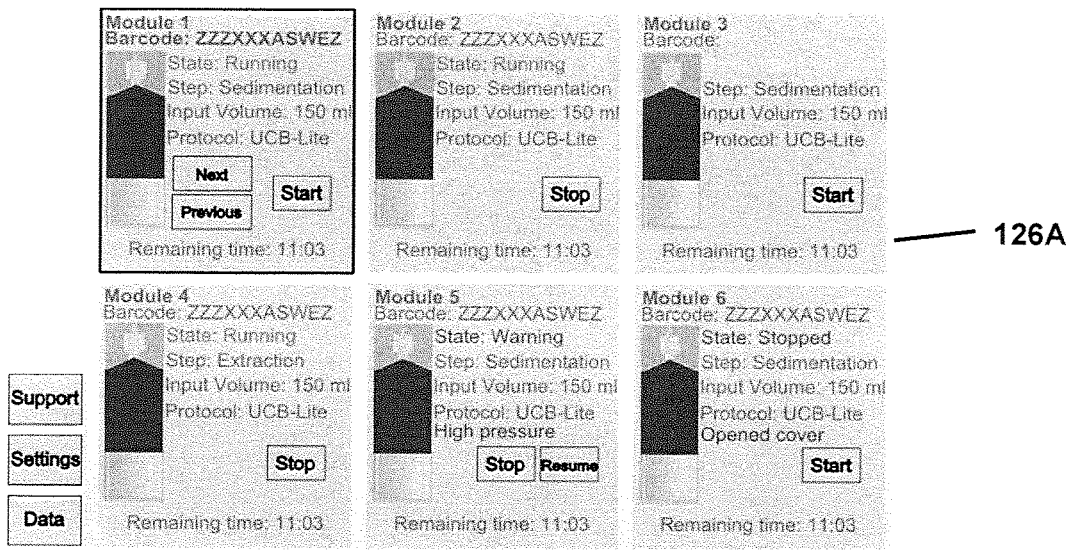
FIGS. 15A and 15B are screenshots of a touch screen showing an overall control panel for all processing units of an apparatus according to the invention and a single control panel for one processing unit.

Each disposable set preferably carries a code bar identifying the contents of the flexible container 200. The code bar can be read by a hand-held code bar reader. The read information is supplied to the central processing unit of the apparatus. The code bar is indicated on the unit's control screen (FIG. 15A).

FIGS. 10A to 10D illustrate some of the possible connections with the apparatus according to the invention. In these Figures a plurality (three for example) of disposable sets each with a processing bag 200 and a centrifugal processing chamber 20 are connected in an apparatus according to the invention in different ways by selective actuation of the electromagnetically-operable pinch valves 124. The positions of the electromagnetically-operated pinch valves 124 are indicated by circles.

Figure 10A:
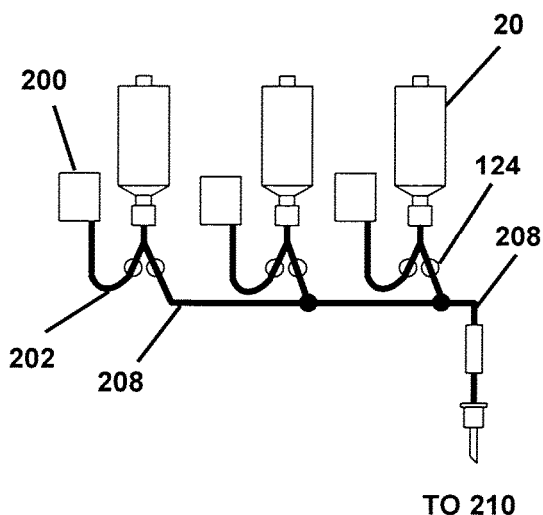
FIGS. 10A, 10B, 10C and 10D are diagrams illustrating different possibilities for connecting flexible containers of the disposable sets.

In FIG. 10A the branches 208 of the different disposable sets are connected in series to a common single blood bag 210 for the three processing units each with a biological fluid bag 200. A typical use would be large volumes to be volume reduced and collected in multiple conservation bags.

Figure 10B:
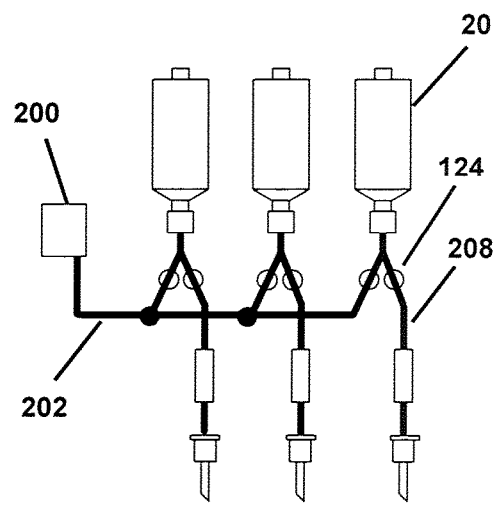

In FIG. 10B the branches 208 of the different disposable sets are connected each to a dedicated blood bag 210 (one blood bag 210 for one centrifugal processing chamber 20), whereas the branches 202 of the different disposable sets are connected in series to the centrifugal processing chambers 20. A typical use would be the processing of several cultured independent cell products than need to be volume reduced and then gathered in the same final solution, like a volume reduction followed by a biological additives addition, followed by a washing procedure.

Figure 10C:
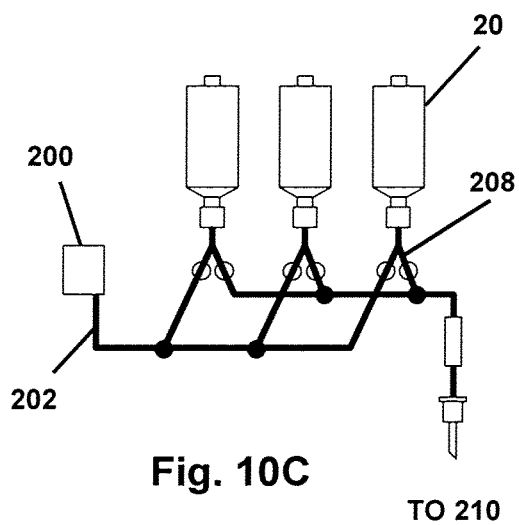

FIG. 10C shows a parallel connection of a single biological fluid bag 200 to a single blood bag 210 via a parallel connection of the branches 202 and 208 to three centrifugal processing chambers 20. A typical use would the parallel processing of large solutions than need to be volume reduced and then collected in the same bag.

Figure 10D:
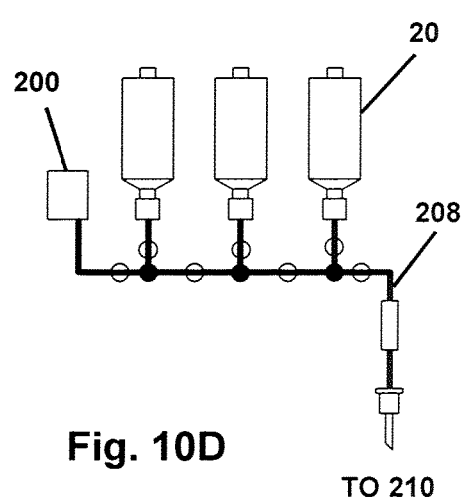

FIG. 10D shows a single biological fluid bag 200 connected in series with three centrifugal processing chambers 20 and a single blood bag 210.

Figure 15B:
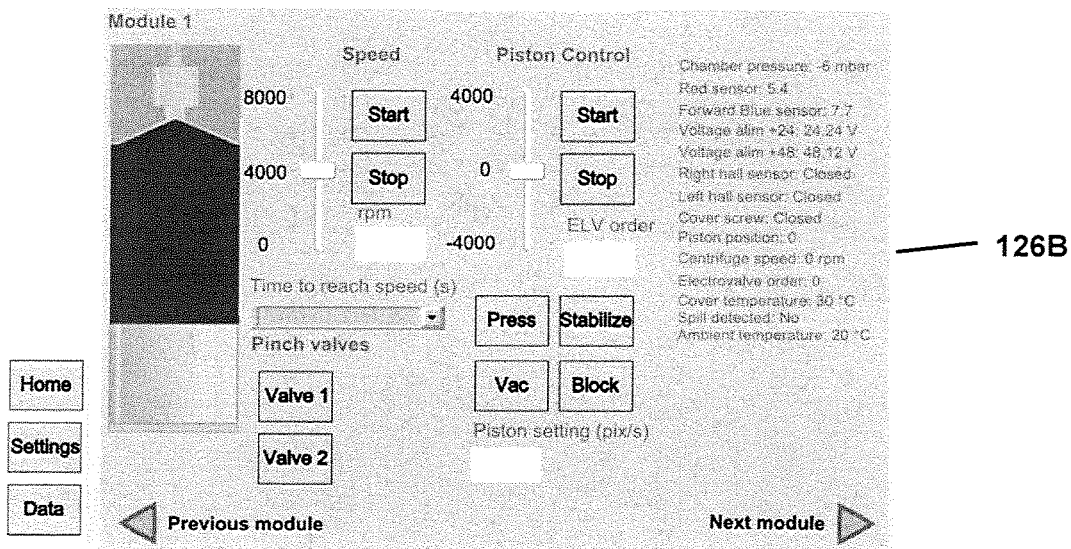

In all of the configurations of connection shown in FIGS. 10A to 10D, the processing chambers 20 are of course inserted in the apparatus' cabinet 100, and the configuration is set up by the operator controlling the opening or closing of the electromagnetically-operated pinch valves 124 of the respective processing units by selection from a menu/protocol displayed on the touch screen 126 (see FIGS. 15A and 15B).

Figure 11:
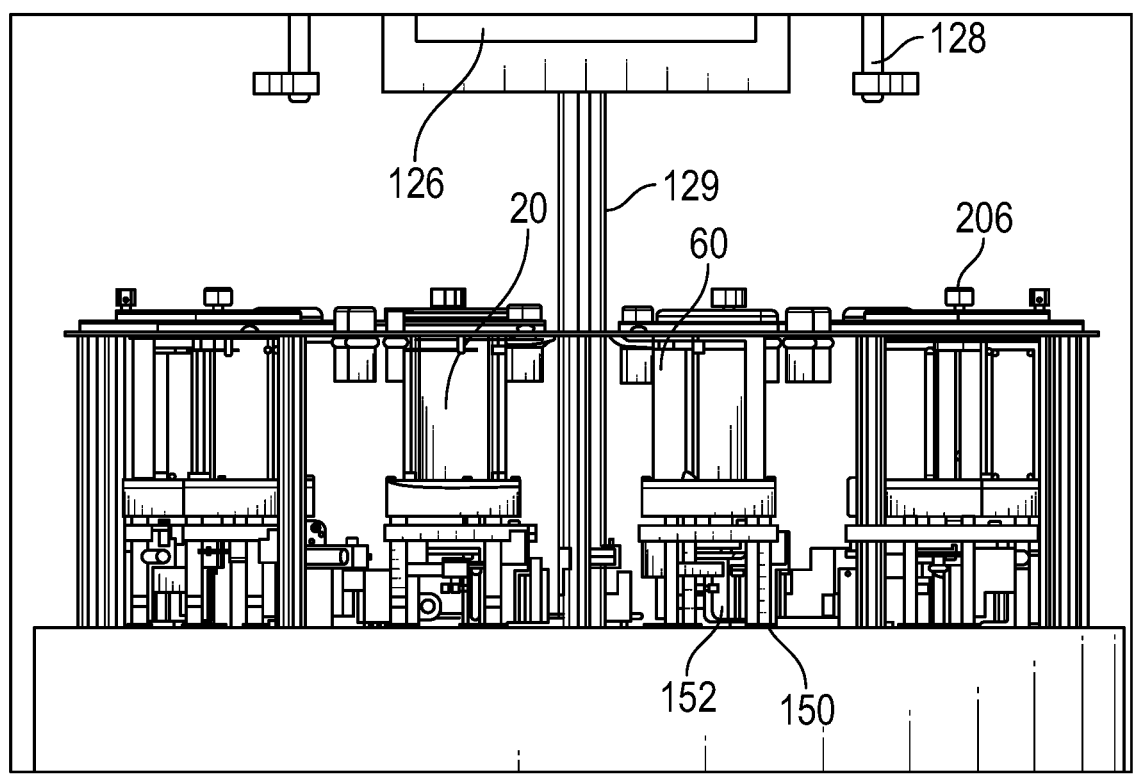
FIG. 11 is a view of the apparatus according to the invention with the cabinet removed to show the internal configuration.

FIG. 11 shows the inside of an apparatus according to the invention after removal of the sidewall 108. Each centrifugal processing chamber 20 is mounted on an open-frame support 150 enclosing a drive unit 152 for the centrifugal processing chamber 20 and all necessary hardware. Beside the location of the centrifugal processing chamber 20 is a position detector 60 as described in EP-B-0 912 250.

Figure 12:
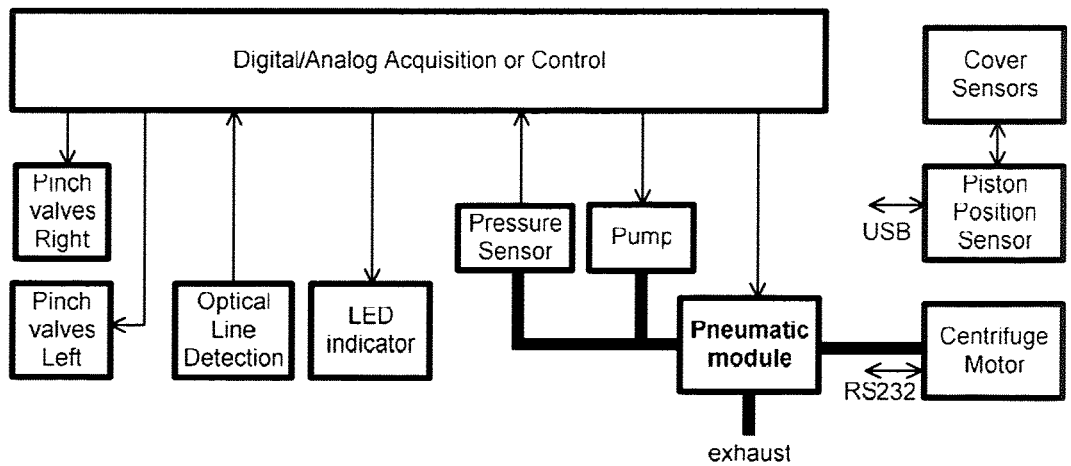
FIG. 12 is a block diagram of circuitry for controlling the system according to the invention.

A block diagram of the circuitry for controlling the apparatus according to the invention is given in FIG. 12. This comprises a control for the pinch valves 124, right and left. This is accomplished by selection from a menu displayed on the touch screen 126 with on/off controls for each magnetically-operable pinch valve 124. The optical line detection is connected to the optical line detectors 122 which detect parameters of the fluid flowing in branch 212 of the tubing. The LED indicator can display several colors and is useful for providing information to users, like "process ongoing", "user intervention required" or "module ready for new procedure". The pneumatic module is connected to a pressure sensor of the fluid in the centrifugal processing chamber 20 and to a pump. This pneumatic module also controls the centrifuge motor of centrifugal processing chamber 20. There is furthermore a piston position sensor that detects the position of the piston (movable member) in the centrifugal processing chamber 20. Cover sensors verify if the covers 114 are open or closed.

Figure 13:
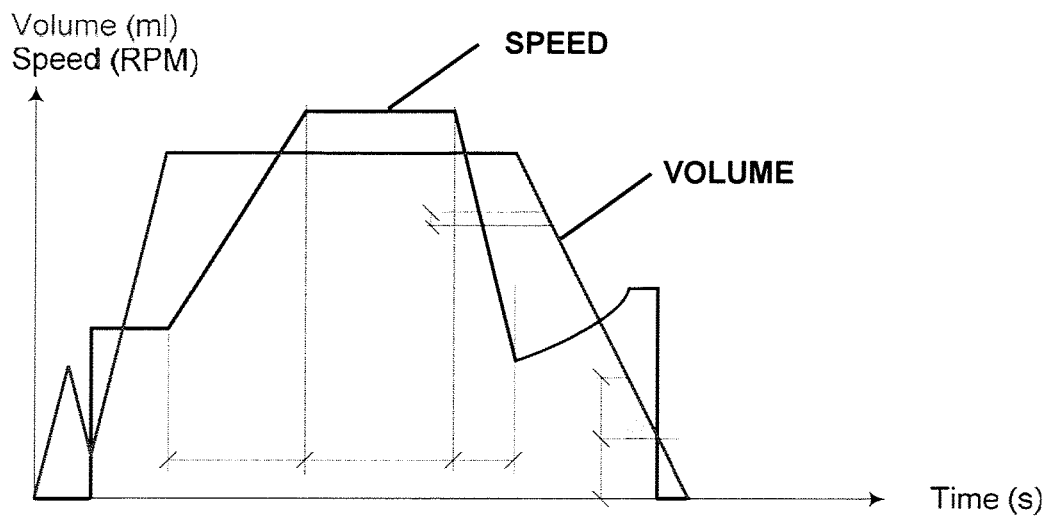
FIG. 13 a diagram illustrating the profile of a protocol for processing a biological fluid.
Figure 14:
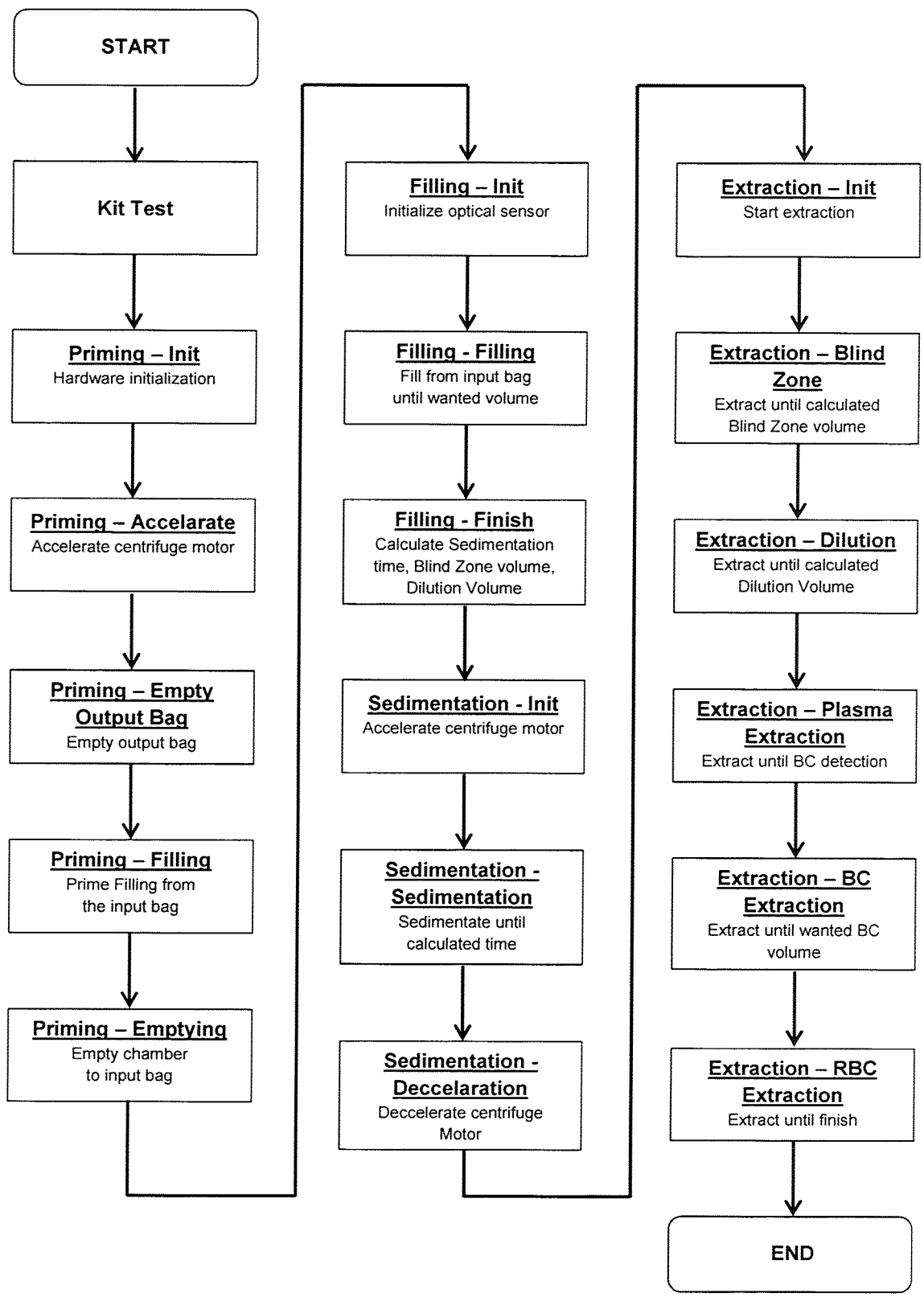
FIG. 14 is a flow diagram corresponding to the profile of FIG. 13.

FIG. 13 illustrates the profile for an operating sequence of a centrifugal processing chamber in an apparatus according to the invention. The profile shows the evolution of the speed of the centrifugal processing chamber 20 in rpm and the sample volume in ml as a function of the operating time in seconds. The corresponding steps of a simplified protocol from start to end are set out in the flow diagram of FIG. 14, including a testing phase for verifying the correct insertion and good working of the disposable kit inserted in the system, a priming phase for volume insertion, a sedimentation phase for separating biological specimens in components and finally extraction steps for separating biological components. The customized profile per biological unit processed keeps the g force constant where the cells are during the extraction.

FIGS. 15A and 15B show screenshots 126A and 126B that are visible on the touchscreen control 126. Screenshot 126A shows details of the six units (referred to as Modules 1 to 6) associated with the centrifugal processing chambers 20 placed in the six locations 110 on the cabinet top 106. For each of the six Modules there is displayed information about the respective Module starting with its barcode and including data on the current state of operation, Stop and Start controls, and controls to proceed to the Next or to the Previous Module. Screenshot 126B shows data and settings for an individual Module, including rotational speed of the centrifugal processing chamber 20 associated with the Module. The rotational speed can be selected on a sliding scale for 0 to 8000 rpm. Also shown is the piston control from −4000 to +4000 units and other controls. The controls «Valve 1» and «Valve 2» enable the operator to set the eletromagnetically-operable pinch valves 124 open or closed. By doing this for all of the Modules, the operator sets up the connections between the disposable sets and blood or additive bags 210. Control of the apparatus configuration is thus simple and user friendly.

A typical serial-chain processing example with the system according to the invention would be a chain of volume reduction of cord blood from 220 ml to 100 ml in a 20 minutes processing cycle, followed by an incubation phase of 30 minutes including the addition of a biological additive and finally followed by a washing processing cycle with Sodium Chloride during an extra 20 minutes.

A parallel processing example with the system according to the invention would include the volume reduction of 3 liters of cell cultured products down to 100 ml including a final washing cycle, with the entire process done in less than 1 hour.

The invention claimed is:

1. A system for processing and separating biological fluids comprising:
   an apparatus comprising,
   (a) a plurality of disposable sets, each disposable set comprising,
      (i) a set of interconnected flexible containers for receiving biological fluid to be separated;
      (ii) a centrifugal processing chamber configured to receive the biological fluid from the set of flexible containers; and
      (iii) a tubing associated with a plurality of remotely actuable pinch valves, the tubing connecting the set of flexible containers to the centrifugal processing chamber; and
   (b) a cabinet comprising a plurality of side-by-side housing locations for housing the respective centrifugal processing chambers of the plurality of disposable sets;
      wherein each respective centrifugal processing chamber of the plurality of disposable sets is housed in a respective housing location of the plurality of housing locations and in a side-by-side spaced apart relation,
      wherein each respective housing location comprises an individual drive means for driving the respective centrifugal processing chamber about its central axis of rotation,
      wherein, the remotely actuable pinch valves are arranged on a surface of the cabinet such that at each housing location of the plurality of housing locations of the respective centrifugal processing chamber of each disposable set of the plurality of disposable sets, two remotely actuable pinch valves are associated with the respective centrifugal processing chamber of each disposable set, the association allowing the two remotely actuable pinch valves to selectively control the input and extraction of the fluid between the respective centrifugal processing chamber and the set of flexible containers of each disposable set via the tubing, wherein, the plurality of disposable sets operate in parallel, as the remote actuation of the pinch valves facilitates a selective transfer of the biological fluid between the set of flexible containers and the centrifugal processing chamber of each disposable set, and wherein the system further comprises valve-actuating means for actuating the remotely actuable pinch valves individually and by combinations of individual actuations, the valve-actuating means comprising a control panel that provides a display of the state of actuation whether open or closed of respective remotely actuable pinch valves, the selection of the state of actuation of the respective remotely actuable pinch valves being arranged to control connection of the respective centrifugal processing chamber of each fitted disposable set with one of the flexible container of the same disposable set or to another container, and to control connection of the respective centrifugal processing chamber with the flexible containers or other containers of several fitted disposable sets in different combinations.

2. The system of claim 1, wherein the tubing connecting the centrifugal processing chambers is in Y-configuration.

3. The system of claim 2, wherein the Y-configuration is characterized by a stem of the tubing being connected to the centrifugal processing chamber, an extremity of one branch of the tubing being connected to a first container of the set of flexible containers, and an extremity of a second branch of the tubing being connected to a second container of the set of flexible containers.

4. The system of claim 3, wherein each of the branches of the tubing has plurality of zones that pass through the remotely-actuable pinch valves.

5. The system of claim 4, wherein the plurality of zones is closable by actuation of the remotely-actuable pinch valves.

6. The system of claim 4, wherein the zones are located adjacent to where the branches of the tubing are branched to the stem of the tubing.

7. The system of claim 6, wherein each processing chamber further comprises a location having a module.

8. The system of claim 7, wherein each module is part of a chain processing event, each module having a dedicated role in the processing of a biological fluid.

9. The system of claim 8, wherein the chain processing event is further characterized by a sequential transfer of biological fluid from one module to another module.

10. The system of claim 1, wherein the valve-actuating means has four different operational arrangements for controlling the remotely actuable valves.

11. The system of claim 10, wherein the valve-actuating means is arranged to provide individual control of the plurality of valves associated with at least one or all disposable sets of the plurality of disposable sets, whose centrifugal processing chambers are received in the cabinet, the arrangement allowing for the separate control of an inlet and outlet of fluid from the flexible containers of each disposable set.

12. The system of claim 11, wherein the valve-actuating means is arranged to provide control of the plurality of pinch valves associated with at least two disposable sets, or all disposable sets of the plurality of disposable sets whose centrifugal processing chambers are received in the cabinet, the arrangement allowing for a connection in series the outlet of at least one flexible container of the disposable sets received in the cabinet to the inlet of another flexible container.

13. The system of claim 12, wherein the valve-actuating means is arranged to provide control of the plurality of pinch valves associated with at least two disposable sets, or all disposable sets of the plurality of disposable sets whose centrifugal processing chambers are received in the cabinet, the arrangement allowing for a connection of the outlet of all but one flexible container of the disposable sets received in the cabinet to the inlet of another flexible container.

14. The system of claim 13, wherein the valve-actuating means is arranged to provide control of the plurality of pinch valves associated with at least two disposable sets, or all disposable sets of the plurality of disposable sets whose centrifugal processing chambers are received in the cabinet, the arrangement allowing for the connection in parallel of the inlets and outlets of each disposable set.

15. The system of claim 14, wherein the arrangements occur in any combination with respect to each other.

16. The system of claim 1, wherein the pinch valves are electro-magnetically actuable pinch valves.

17. The system of claim 16, wherein the electro-magnetically actuable pinch valves are located on a top surface of the cabinet in the proximity of a plurality of locations for receiving the centrifugal processing chambers.

18. The system of claim 3, wherein an outer surface of the top of the cabinet comprises an array of projections provided with a plurality of through-openings for guiding the tubing of the flexible containers.

19. The system of claim 18, wherein the top of the cabinet optionally comprises a visible guide line.

20. The system of claim 19, wherein the guide line is located between and adjacent to the array of projections and defines a path for the tubing of the flexible container.

21. The system of claim 20, wherein the tubing of the flexible container comprises a path that passes through the array of projections.

22. The system of claim 17, wherein the top of the cabinet further comprises a first projection adjacent to each location for receiving the processing chamber, the first projection having a diametral groove for receiving the tubing on a top surface.

23. The system of claim 22, wherein the first projection further comprises an optical line sensor.

24. The system of claim 22, wherein the top of the cabinet further comprises two second projections, each second projection incorporating the electromagnetically-actuable pinch valve.

25. The system of claim 24, wherein the second projections each have a flat face with a lateral through-groove for receiving a tubing.

26. The system of claim 24, wherein the first projection and the two second projections are located along a generally Y-shaped path for the tubing along the top of the cabinet.

27. The system of claim 1, wherein the cabinet has a substantially flat top and a generally upright outer wall.

28. The system of claim 27, wherein the outer wall comprises a series of recesses in an upper part of the cabinet.

29. The system of claim 28, wherein the recesses are shaped and configured to receive and support the flexible container of a disposable set located on the outer upper wall of the cabinet.

30. The system of claim 29, wherein the cabinet has a D shape in a horizontal section, with a curved outer wall along which, and adjacent to which, the locations for the processing chambers are distributed.

31. The system of claim 1, wherein the cabinet further comprises a flat rear wall.

32. The system of claim 1, further comprising two upright poles.

33. The system of claim 32, wherein the poles extend above and generally to the rear of the cabinet.

34. The system of claim 32, wherein the poles have a plurality of hooks for suspending the containers of biological fluid to be treated.

35. The system of claim 32, wherein the control panel further comprises a touch-screen command arranged between the two poles by a central post extending up from the cabinet.

36. The system of claim 1, wherein the cabinet comprises a plurality of four to fifteen locations for the centrifugal processing chambers.

37. The system of claim 36, wherein the cabinet comprises a plurality of six to twelve locations for the processing chambers.

38. The system of claim 11, wherein the system is arranged to operate in a separation mode and in a non-separation transfer mode.

39. The system of claim 38, wherein in separation mode:
(a) the fluid is transferred into at least one processing chamber while the chamber is rotating or stationary;
(b) the fluid is centrifuged and separated into components; and
(c) the separated components are expressed while the chamber is rotating or, optionally, for the last separated component, while the chamber is stationary.

40. The system of claim 38, wherein in the non-sequential transfer mode:
(a) at least one processing chamber intakes the fluid and expresses the fluid with the chamber stationary; and
(b) the valve-actuation arrangement transfers fluid from one container to another via the processing chamber.

41. The system of claim 40, wherein the processing chamber comprises an axially movable member.

42. The system of claim 41, wherein the axially movable member includes a sensor means for monitoring the position of the axially movable member.

43. The system of claim 40, wherein the transfer of fluid from one container to another container is characterized by the movement of the member axially without centrifugation or separation of the fluid into components.

44. The system of claim 42, wherein the sensor means for monitoring the position of the axially movable member controls the amount of non-separated fluids transferred.

* * * * *